(12) United States Patent
Hayakawa

(10) Patent No.: US 8,409,551 B2
(45) Date of Patent: Apr. 2, 2013

(54) WATER-RELEASING COSMETIC MAKEUP MATERIAL

(75) Inventor: Chihiro Hayakawa, Yokohama (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/078,025

(22) Filed: Apr. 1, 2011

(65) Prior Publication Data
US 2011/0256077 A1 Oct. 20, 2011

(30) Foreign Application Priority Data
Apr. 14, 2010 (JP) .................. 2010-093563

(51) Int. Cl.
*A61K 8/894* (2006.01)
*A61Q 1/02* (2006.01)
*A61Q 17/04* (2006.01)

(52) U.S. Cl. .................. 424/60; 424/63; 424/78.03

(58) Field of Classification Search .................. 424/60, 424/63, 78.03
See application file for complete search history.

(56) References Cited

U.S. PATENT DOCUMENTS

| | | | | |
|---|---|---|---|---|
| 5,635,163 | A | * | 6/1997 | Hansenne ................ 424/60 |
| 7,378,103 | B2 | * | 5/2008 | Kanji et al. .............. 424/401 |
| 2003/0064046 | A1 | | 4/2003 | Omura et al. |
| 2007/0059263 | A1 | * | 3/2007 | Taniguchi et al. ......... 424/63 |
| 2011/0028571 | A1 | * | 2/2011 | Hayakawa ............. 514/772.4 |

OTHER PUBLICATIONS

Ikeda, "Fragrance Journal," Fragrance Journal, Ltd., vol. 37, No. 2, pp. 19-26, 2009 (with partial English translation).

* cited by examiner

*Primary Examiner* — Aradhana Sasan
(74) *Attorney, Agent, or Firm* — Birch, Stewart, Kolasch & Birch, LLP

(57) ABSTRACT

A water-releasing cosmetic makeup material that has excellent stability, exhibits good dispersion of color pigments, and ruptures smoothly upon application to provide good spreadability and superior feeling. The water-releasing cosmetic makeup material is formed of a water-in-oil emulsion comprising (a) a partially crosslinked polyether-modified silicone, a partially crosslinked polyglycerin-modified silicone, or a combination thereof, (b) an acrylic silicone-based graft copolymer, and (c) a branched silicone surfactant in an amount of 0.05 to 0.7% by mass.

10 Claims, No Drawings

WATER-RELEASING COSMETIC MAKEUP MATERIAL

BACKGROUND OF THE INVENTION

1. Field of the Invention

The present invention relates to a water-in-oil type water-releasing cosmetic makeup material.

2. Description of the Prior Art

Partially crosslinked polyether-modified silicones exhibit higher water retention and yield emulsions having larger particle sizes than conventional surfactants, and are known to yield cosmetic materials that exhibit a favorable feeling of wetness and a light touch (Patent Document 1 and Non-patent Document 1). Further, it is also known that water-releasing type cosmetic materials can be prepared by using these types of modified silicones. In this description, the term "water-releasing" describes the phenomenon wherein, upon application of a cosmetic material, the shearing forces generated by the application cause the water-in-oil type emulsion to rupture, thereby causing the internal water phase to burst out in the form of water droplets.

These types of water-releasing cosmetic materials require the design of an emulsion having large emulsion particles, and because the size of the emulsion particles tends to decrease if a large amount of a linear or branched surfactant such as a linear or branched polyether-modified silicone is used, the development of water-releasing cosmetic materials has proven to be difficult.

On the other hand, in the case of cosmetic makeup materials such as foundations, a color pigment is added. In order to ensure good stability and prevent color variation for these color pigments, a suitable amount of a surfactant must be added, but because this surfactant also has the effect of reducing the emulsion particle size within the emulsion, the development of water-releasing cosmetic makeup materials has also proven difficult.

Moreover, in those cases where an ultraviolet protection effect is to be imparted to a cosmetic makeup material, an organic ultraviolet protective agent such as ethylhexyl methoxycinnamate is typically used, but these types of organic ultraviolet protective agents exhibit poor compatibility with dimethicone and polyether-modified silicones and the like, meaning there is a limit to how much may be added. This problem further complicates the design of water-releasing cosmetic makeup materials.

Furthermore, if the viscosity of the oil phase is increased too much in an attempt to raise the stability of the cosmetic material, then problems tend to arise, such as greater difficulty in spreading the burst water droplets across the skin. Accordingly, designing a water-releasing cosmetic makeup material that is stable and yet exhibits a pleasing feeling on the skin has proven to be very difficult.

PRIOR ART DOCUMENTS

Patent Documents

Patent Document 1: US 2003/0064046 A1

Non-Patent Documents

Non-Patent Document 1: Ikeda, Fragrance Journal, 37(2), 24 (2009)

SUMMARY OF THE INVENTION

Accordingly, the development of a water-releasing cosmetic makeup material that has excellent stability, exhibits good dispersion of color pigments, and ruptures smoothly upon application to provide good spreadability and superior feeling has been keenly sought.

As a result of intensive investigation aimed at addressing the issues outlined above, the inventors of the present invention discovered that a water-releasing cosmetic makeup material formed of a water-in-oil emulsion comprising:

(a) a partially crosslinked polyether-modified silicone, a partially crosslinked polyglycerin-modified silicone, or a combination thereof, (b) an acrylic silicone-based graft copolymer, and (c) a branched silicone surfactant in an amount of 0.05 to 0.7% by mass was able to address the above issues, and they were therefore able to complete the present invention.

The water-releasing cosmetic makeup material of the present invention has excellent stability, exhibits good dispersion of color pigments, and has an emulsion state that ruptures smoothly upon application to provide good spreadability and superior feeling.

DETAILED DESCRIPTION OF THE PREFERRED EMBODIMENTS

A more detailed description of the water-releasing cosmetic makeup material of the present invention is presented below.

<Component (a)>

The component (a) of the present invention is a partially crosslinked polyether-modified silicone, a partially crosslinked polyglycerin-modified silicone, or a combination thereof. Conventional materials may be used as the partially crosslinked polyether-modified silicone and the partially crosslinked polyglycerin-modified silicone.

Partially crosslinked polyether-modified silicones are three-dimensional crosslinked materials in which organopolysiloxane chains have been crosslinked via polyether chains. Specific examples of these partially crosslinked polyether-modified silicones include materials referred to using the names (dimethicone/(PEG-10/15)) crosspolymer, (PEG-15/lauryl dimethicone) crosspolymer and (PEG-15/lauryl polydimethylsiloxyethyl dimethicone) crosspolymer. These materials are available commercially in a form of being swollen with and containing a silicone or other oils, and are marketed under product names such as KSG-210, 240, 310, 340 and 320Z (all manufactured by Shin-Etsu Chemical Co., Ltd.).

Further, partially crosslinked polyglycerin-modified silicones are three-dimensional crosslinked materials in which organopolysiloxane chains have been crosslinked via polyglycerin chains. Specific examples of these partially crosslinked polyglycerin-modified silicones include materials referred to using the names (dimethicone/polyglycerin-3) crosspolymer, (lauryl dimethicone/polyglycerin-3) crosspolymer, and (polyglyceryl-3/lauryl polydimethylsiloxyethyl dimethicone) crosspolymer. These materials are available commercially as gels containing silicone oils and other oils, and are marketed under product names such as KSG-710, 810 and 820Z (all manufactured by Shin-Etsu Chemical Co., Ltd.).

The blend amount of the component (a) within the water-releasing cosmetic makeup material of the present invention is preferably within a range from 0.5 to 1.5% by mass. If this blend amount is too small, then the stability of the emulsion may deteriorate or the material may become difficult to emulsify, whereas if the blend amount is too large, then the viscosity of the oil phase tends to increase, which may result in a cosmetic material having poor feeling upon application.

<Component (b)>

Conventional materials may be used as the acrylic silicone-based graft copolymer of the component (b) of the present invention.

This copolymer is a graft polymer in which dimethylpolysiloxane chains are grafted onto an acrylic polymer chain.

These types of graft copolymers are mainly known as film-forming agents, with names such as (alkyl acrylate/dimethicone) copolymer, and are available commercially under product names such as KP-545, 549 and 550 (all manufactured by Shin-Etsu Chemical Co., Ltd.) in the form of solutions within volatile solvents such as isododecane, decamethylcyclopentasiloxane, methyltrimethicone and dimethicone (low-molecular weight materials having a viscosity at 25° C. of not more than 2 mm²/s). In terms of the monomers used in preparing these acrylic silicone-based graft copolymer, monomers in which the carboxyl group of acrylic acid or the like has been esterified yield copolymers with reduced levels of acrylic odor, and are consequently preferred.

The blend amount of the component (b) within the cosmetic material of the present invention is preferably within a range from 0.3 to 1.5% by mass.

<Component (c)>

Conventional materials may be used as the branched silicone surfactant of the component (c) of the present invention. This surfactant is a lipophilic surfactant having a structure in which hydrophilic polymer chains are grafted to a branched hydrophobic silicone chain. There are no particular limitations on the hydrophilic polymer chains, and for example, polymer chains formed of polyethers or polyglycerins or the like may be used.

Examples in which the hydrophilic polymer chains are polyethers include silicone compounds disclosed in JP 2001-39819 A (or U.S. Pat. No. 6,576,623), represented by general formula (1):

$$R^1_a R^2_b R^3_c SiO_{(4-a-b-c)/2} \quad (1)$$

[wherein each $R^1$ represents an identical or different organic group selected from the group consisting of alkyl groups, aryl groups, aralkyl groups and fluorine-substituted alkyl groups of 1 to 30 carbon atoms, and organic groups represented by general formula (2):

$$—C_mH_{2m}—O—(C_2H_4O)_d(C_3H_6O)_eR^4 \quad (2)$$

$R^2$ represents a polyoxyalkylene group represented by general formula (3):

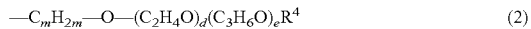

$$—C_mH_{2m}—O—(C_2H_4O)_f(C_3H_6O)_g—R^5 \quad (3)$$

$R^3$ represents an organosiloxane residual group represented by general formula (4) below:

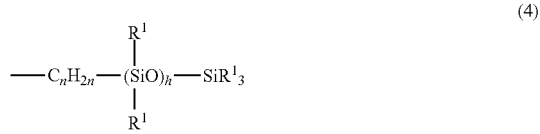

(4)

$$—C_nH_{2n}—(SiO)_h—SiR^1_3$$
with $R^1$ groups on the silicon $R^4$ represents a hydrogen atom, a hydrocarbon group of 4 to 30 carbon atoms or an organic group represented by $R^6$—(CO)—, $R^5$ represents a hydrogen atom, a hydrocarbon group of 1 to 30 carbon atoms or an organic group represented by $R^6$—(CO)—, and $R^6$ represents a hydrocarbon group of 1 to 30 carbon atoms, a, b and c are numbers that satisfy the ranges $1.0 \leq a \leq 2.5$, $0.001 \leq b \leq 1.5$, and $0.001 \leq c \leq 1.5$ respectively, d and e are integers that satisfy the ranges $0 \leq d \leq 50$ and $0 \leq e \leq 50$ respectively, f and g are integers that satisfy the ranges $2 \leq f \leq 200$ and $0 \leq g \leq 200$ respectively, provided that f+g satisfies a range of 3 to 200, m represents an integer that satisfies $0 \leq m \leq 15$, h represents an integer that satisfies $0 \leq h \leq 500$, and n represents an integer that satisfies $1 \leq n \leq 5$].

A more detailed description of general formula (1) is presented below. Each $R^1$ represents an identical or different organic group selected from the group consisting of alkyl groups, aryl groups, aralkyl groups and fluorine-substituted alkyl groups of 1 to 30 carbon atoms, and specific examples of these groups include alkyl groups such as a methyl group, ethyl group, propyl group, butyl group, pentyl group, hexyl group, heptyl group, octyl group, nonyl group and decyl group, cycloalkyl groups such as a cyclopentyl group and cyclohexyl group, aryl groups such as a phenyl group and tolyl group, aralkyl groups such as a benzyl group and phenethyl group, and fluorine-substituted alkyl groups such as a trifluoropropyl group and heptadecafluorodecyl group.

Further, $R^1$ may also represent an alkoxy group, ester group, alkenyl ether residual group or alkenyl ester residual group represented by general formula (2): —$C_mH_{2m}$—O—$(C_2H_4O)_d(C_3H_6O)_nR^4$. In formula (2), $R^4$ represents a hydrogen atom, a monovalent hydrocarbon group of 4 to 30 carbon atoms or an organic group represented by $R^6$—(CO)—. Examples of the monovalent hydrocarbon group of 4 to 30 carbon atoms represented by $R^4$ and the hydrocarbon groups of 1 to 30 carbon atoms represented by $R^5$ and $R^6$ include the same groups as those listed above for $R^1$. Further, d and e each represents an integer of 0 to 50, and m represents an integer of 0 to 15.

For example, in those cases where m, d and e each represents 0, general formula (2) represents a silanol or an alkoxy group of 1 to 30 carbon atoms, specific examples of which range from lower alkoxy groups such as a methoxy group or ethoxy group through to higher alkoxy groups such as an oleyloxy group or stearoxy group. Alternatively, $R^1$ may represent an ester group of acetic acid, lactic acid, butyric acid, oleic acid, stearic acid or behenic acid or the like.

Further, among those cases where m represents 1 or more and d and e each represents 0, groups in which m represents 3, 5 or 11 are particularly preferred. In these cases, $R^1$ represents an allyl ether residual group, a pentenyl ether residual group or an undecenyl ether residual group, and depending on the nature of the $R^4$ substituent, examples of the resulting $R^1$ group include an allyl stearyl ether residual group, a pentenyl behenyl ether residual group or an undecenyl oleyl ether residual group. If d or e is not 0, then $R^1$ becomes an alkoxy group or ester group that is linked via a polyoxyalkylene.

The values of d and e may be any number, but if m is 0, then the resulting surfactant may suffer from poor hydrolysis resistance, whereas if m is 15 or greater, then the surfactant tends to have a strong oily odor, and consequently m is preferably within a range from 3 to 5. In the present invention, it is particularly desirable that at least 50% of all the $R^1$ groups in formula (1) are methyl groups, and compounds in which 70% or more of the $R^1$ groups are methyl groups are even more preferred. In some cases, 100% of the $R^1$ groups may be methyl groups.

The above-mentioned $R^2$ is a polyoxyalkylene group represented by general formula (3): —$C_mH_{2m}$—O—$(C_2H_4O)_f(C_3H_6O)_g$—$R^5$. In this formula (3), $R^5$ represents a hydrogen atom, a hydrocarbon group of 1 to 30 carbon atoms or an organic group represented by $R^6$—(CO)—, wherein $R^6$ represents a hydrocarbon group of 1 to 30 carbon atoms. f represents an integer of 2 to 200, and preferably 5 to 100, and g represents an integer of 0 to 200, and preferably 0 to 100, provided that f+g is an integer of 3 to 200, and preferably 5 to 100. In order to impart sufficient hydrophilicity to obtain a satisfactory water-in-oil emulsion, it is preferable that f/g≧1. In those cases where the polyoxyalkylene portion within formula (3) is composed of both ethylene oxide units and propylene oxide units, the polyoxyalkylene may be either a block polymer or a random polymer of these two units.

$R^3$ in formula (1) represents an organosiloxane residual group represented by the above general formula (4). In general formula (4), h represents an integer of 0 to 500, and preferably 3 to 100. n represents an integer of 1 to 5, and in those cases where synthesis is performed using a reaction between a vinyl group and a hydrogensiloxane, n is 2. If h is greater than 500, then problems may arise, such as a deterioration in the reactivity with the hydrogensiloxane of the main chain.

a represents a number within a range from 1.0 to 2.5, and preferably from 1.2 to 2.3. If a is less than 1.0, then because the compatibility with oil agents tends to deteriorate, forming a stable water-in-oil emulsion becomes difficult, whereas if a is greater than 2.5, then the resulting hydrophilicity is poor, which also makes forming a stable water-in-oil emulsion difficult. b represents a number within a range from 0.001 to 1.5, and preferably from 0.05 to 1.0. If b is less than 0.001, then the resulting hydrophilicity is poor, and therefore forming a stable water-in-oil emulsion is difficult, whereas if b is greater than 1.5, then the hydrophilicity tends to become too high, which also makes forming a stable water-in-oil emulsion difficult. c represents a number within a range from 0.001 to 1.5, and preferably from 0.05 to 1.0. If c is less than 0.001, then because the compatibility with the silicone oil tends to be poor, forming a stable water-in-oil emulsion becomes difficult, whereas if c is greater than 1.5, then the resulting hydrophilicity is poor, which also makes forming a stable water-in-oil emulsion difficult.

As an emulsifier, there are no particular limitations on the weight average molecular weight of the silicone compound represented by general formula (1), but a weight average molecular weight of 500 to 200,000 is preferred, and a value of 1,000 to 100,000 is particularly desirable.

The silicone compound of general formula (1) can be produced using the method disclosed in the above-mentioned JP 2001-39819 A.

Of the various possible forms of the component (c), surfactants in which the above-mentioned hydrophilic polymer chain is composed of a polyether are known by names such as PEG-9 polydimethylsiloxyethyl dimethicone and lauryl PEG-9 polydimethylsiloxyethyl dimethicone, and can be obtained commercially under product names such as KF-6028, KF-6028P and KF-6038 (all manufactured by Shin-Etsu Chemical Co., Ltd.). Further, surfactants in which the hydrophilic polymer chain is composed of a polyglycerin are known by names such as polyglyceryl-3 polydimethylsiloxyethyl dimethicone and lauryl polyglyceryl-3 polydimethylsiloxyethyl dimethicone, and can be obtained commercially under product names such as KF-6104 and KF-6105 (all manufactured by Shin-Etsu Chemical Co., Ltd.).

Of these, those surfactants that do not have long-chain alkyl groups bonded to the hydrophobic silicone chain, such as PEG-9 polydimethylsiloxyethyl dimethicone and polyglyceryl-3 polydimethylsiloxyethyl dimethicone, are preferred. These' types of surfactants exhibit excellent compatibility with silicone oils, phenyl-modified silicones, and low-viscosity ester oils.

These branched silicone surfactants of the component (c) are blended into the cosmetic material in an amount of 0.05 to 0.7% by mass. If the blend amount is too small, then the cosmetic material becomes prone to a loss in stability when subjected to impacts or shearing forces during transport or production, whereas if the blend amount is too large, then the particle size of the emulsion tends to decrease, and the water-releasing property may be lost. It is known that cosmetic materials in which the hydrophilic groups are polyglycerins are less prone to a decrease in the emulsion particle size than cosmetic materials in which the hydrophilic groups are polyethers.

<Optional Components>

Other components besides the components (a) to (c) may be added to the cosmetic material of the present invention according to need.

(d) Ethylhexyl Methoxycinnamate

Adding ethylhexyl methoxycinnamate enables an ultraviolet protective effect to be imparted to the cosmetic material of the present invention.

Ethylhexyl methoxycinnamate is a representative organic ultraviolet protective agent widely known as OMC, and is available commercially, for example, under the product name NOMCORT TAB (manufactured by The Nisshin OilliO Group, Ltd.).

(e) Phenyl-Modified Silicone

In those cases where ethylhexyl methoxycinnamate of the above component (d) is added to the cosmetic material of the present invention, a phenyl-modified silicone is preferably also added to the cosmetic material. By including both the component (d) and the component (e), an ultraviolet protective effect can be imparted to the cosmetic material of the present invention while maintaining the emulsion properties and stability of the cosmetic material.

As mentioned above, the component (e) is preferably added in those cases where the component (d) is added, and in such cases, from the viewpoint of the stability of the emulsion, the blend amount of the ethylhexyl methoxycinnamate of the component (d) is preferably not more than the blend amount of the phenyl-modified silicone of the component (e) on a mass % basis. However, the blend amount of the component (d) can be increased by using a cyclic organosiloxane, for example a low-molecular weight cyclic dimethylsiloxane oligomer such as decamethylcyclopentasiloxane (D5), as an optional volatile solvent.

In this description, the term "phenyl-modified silicone" is a generic term describing silicone oils that contain a phenyl group and are liquid at 25° C., and conventional oils may be used. Examples of commercially available products of such phenyl-modified silicones are known by names such as diphenyl dimethicone, phenyl trimethicone and diphenylsiloxyphenyl trimethicone, and examples of specific product names include KF-53, 54 and 56A (all manufactured by Shin-Etsu Chemical Co., Ltd.).

Of these silicones, diphenylsiloxyphenyl trimethicone has a low viscosity and excellent spreadability, and is consequently preferred.

Other Components

Other optional components besides the above-mentioned components (d) and (e) may also be added to the cosmetic material of the present invention, provided such addition does not impair the effects of the present invention, and example of these other optional components include the types of components typically used within cosmetic materials such as oil agents, powder components, surfactants, thickeners, film-forming agents, ultraviolet absorbers and other medicinal agents.

Oil Agents

There are no particular limitations on the above-mentioned oil agents, provided they are the types of oils typically used in cosmetic materials, and solid, semi-solid or liquid oil agents may be used. Examples of these oil agents include silicone oils, hydrocarbon oils, higher fatty acids, higher alcohol oils, ester oils, animal-based and plant-based oils and fats, semi-synthetic oils and fluorine-based oils.

Examples of the silicone oils include low-viscosity to high-viscosity linear or branched organopolysiloxanes such as dimethylpolysiloxane, caprylyl methicone, cetyl dimethicone and methylhexylpolysiloxane; cyclic organopolysiloxanes such as octamethylcyclotetrasiloxane, decamethylcyclopentasiloxane and dodecamethylcyclohexasiloxane; branched organopolysiloxanes such as tris(trimethylsiloxy)methylsilane and tetrakis(trimethylsiloxy)silane; silicone-modified olefin waxes such as butylpolydimethylsiloxyl(ethylene/propylene/vinylnorbornene) copolymers; as well as amino-modified organopolysiloxanes, pyrrolidone-modified organopolysiloxanes, pyrrolidone carboxylic acid-modified organopolysiloxanes, gum-like dimethylpolysiloxanes having high polymerization degrees, gum-like amino-modified organopolysiloxanes, higher alkoxy-modified organopolysiloxanes such as stearoxysilicones, higher fatty acid-modified organopolysiloxanes, alkyl-modified organopolysiloxanes, long chain alkyl-modified organopolysiloxanes and fluorine-modified organopolysiloxanes.

Linear, branched or cyclic silicone oils that are volatile at room temperature (25° C.), such as octamethyltrisiloxane, decamethyltetrasiloxane, octamethylcyclotetrasiloxane, decamethylcyclopentasiloxane, tris(trimethylsiloxy)methylsilane and tetrakis(trimethylsiloxy)silane are preferably used for a portion of the silicone oil agent.

Examples of the hydrocarbon oils include linear and branched volatile hydrocarbon oils. Specific examples of these hydrocarbon oils include ozokerite, α-olefin oligomers, light isoparaffin, isododecane, light liquid isoparaffin, squalane, synthetic squalane, plant-based squalane, squalene, ceresin, paraffin, paraffin wax, polyethylene wax, polyethylene-polypropylene wax, (ethylene-propylene-styrene) copolymers, (butylene-propylene-styrene) copolymers, liquid paraffin, liquid isoparaffin, pristane, polyisobutylene, hydrogenated polyisobutene, microcrystalline wax and Vaseline.

Specific examples of the higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, POE cholesterol ether, monostearyl glycerin ether (batyl alcohol) and monooleyl glyceryl ether (selachyl alcohol).

Examples of the ester oils include monoesters such as cetyl 2-ethylhexanoate, isononyl isononanoate, isotridecyl isononanoate, 2-ethylhexyl palmitate, octyldodecyl myristate, neopentyl glycol dioctanoate and neopentyl glycol dicaprate; dibasic acid esters such as diisopropyl sebacate and diisostearyl malate; triglycerides such as triethylhexanoin; polyglycerin esters such as polyglyceryl-2 triisostearate; trimethylolpropane derivatives such as trimethylolpropane triisostearate and trimethylolpropane tri-2-ethylhexanoate; phytosterol derivatives such as phytosteryl 12-hydroxystearate and phytosteryl isostearate; amino acid-based esters such as 2-octyldodecyl N-lauroyl-L-glutamate; and fatty acid pentaerythritol esters of hydroxystearic acid and rosin acid and the like, such as dipentaerythritol (hydroxystearate-stearate-rosinate).

Examples of the animal-based and plant-based oils and fats include oils and fats obtained by purifying avocado oil, linseed oil, almond oil, olive oil, ibota wax, cacao fat, carnauba wax, candelilla wax, wheat germ oil, sesame oil, rice germ oil, rice bran oil, safflower oil, shea butter, jojoba oil, squalane, soybean oil, camellia oil, evening primrose oil, corn oil, lard, rapeseed oil, rice bran wax, germ oil, palm kernel oil, castor oil, sunflower oil, macadamia nut oil, beeswax, meadowfoam oil, cottonseed oil, Japan wax, montan wax, peanut oil, lanolin, liquid lanolin and egg-yolk oil. Further, examples of hydrogenated products of these oils and fats include jojoba wax, hardened castor oil, hardened rapeseed oil, and reduced lanolin.

Examples of the fluorine-based oils include perfluoropolyoxyalkylenes, perfluorodecalin and perfluorooctane.

Of these oil agents, oil agents that are liquid at room temperature are preferred, including hydrocarbon oils such as squalane, isododecane and isoparaffin, ester oils having a branched structure such as triethylhexanoin, neopentyl glycol diethylhexanoate, and isotridecyl isononanoate, and silicone oils having a viscosity at room temperature of 2 to 10 cs.

Powder Components

Provided they are the types of powders typically used in cosmetic materials, any powder components may be used, regardless of the particle shape (be it spherical, needle-like, plate-like, resin-like, fibrous or amorphous or the like), particle size or particle structure (be it porous, non-porous, hollow or hollow-porous or the like). Examples of these types of powders include inorganic powders, organic powders, metal soaps and coloring powders. In order to suppress surface activity, improve the dispersibility, and/or improve the feeling obtained upon application of the cosmetic material, these powder components may be surface treated using metal soaps, silica, aluminum oxide, aluminum hydroxide or some other conventional method, or may be used in the form of a complexed powder.

Specific examples of the inorganic powders include ultraviolet absorption and scattering agents such as microparticulate titanium oxide, microparticulate zinc oxide and microparticulate cerium oxide, and extender pigments such as barium sulfate, calcium carbonate, magnesium carbonate, talc, mica, kaolin, sericite, synthetic phlogopite, silica, hydroxyapatite and boron nitride.

Examples of the organic powders include polyester powders, polyethylene powders, polystyrene powders, polyurethane powders, polymethylmethacrylate powders, methyl methacrylate crosspolymers, cellulose powders, silk powders, nylon powders such as 12-nylon and 6-nylon, fibrous powders of the above-mentioned powders, crosslinked silicone fine powders having a crosslinked dimethylpolysiloxane structure, crosslinked spherical polymethylsilsesquioxane fine powders, fine powders prepared by coating the surface of a crosslinked spherical organopolysiloxane rubber with polymethylsilsesquioxane particles, resin layered rubber particles, starch powders, fatty acid starch derivative powders and lauroyl lysine powders.

In particular, by using a powder prepared by coating the surface of a crosslinked spherical organopolysiloxane rubber such as a (vinyl dimethicone/methicone silsesquioxane) crosspolymer or a (diphenyl dimethicone/vinyldiphenyl dimethicone/silsesquioxane) crosspolymer with polymethylsilsesquioxane particles for a portion of the powder, the cosmetic material can be imparted with good dispersibility as well as a superior soft and dry feeling upon application. Specific examples of commercially available products of these powders include KSP-100, KSP-101, KSP-102, KSP-105 and KSP-300 (all manufactured by Shin-Etsu Chemical Co., Ltd.).

Examples of the metal soaps include zinc stearate and aluminum stearate.

Examples of the coloring powders include inorganic coloring pigments such as titanium oxide, iron oxide, titanium black, carbon black, chromium hydroxide, chromium oxide, iron blue, ultramarine and aluminum powder, tar colorants such as Red No. 226 and Yellow No. 4, natural colorants such as carmine, and pearl pigments such as mica titanium, iron oxide-coated mica titanium and titanium oxide-coated synthetic phlogopite.

These powders may be subjected to a surface treatment using one or more commercially available film-forming agents or surface treatment agents, provided the surface treatment does not impair the effects of the present invention. As the surface treatment agent, products such as KF-9908, KF-9909 and KP-574 (all manufactured by Shin-Etsu Chemical Co., Ltd.) yield excellent dispersibility in keeping with the desired purpose.

Surfactants

Surfactants other than the above-mentioned component (c) may be added if required. There are no particular limitations on these surfactants, and any of the types of surfactants used in typical cosmetic materials may be used. These surfactants include anionic, cationic, nonionic and amphoteric surfactants.

Of these surfactants, nonionic surfactants are frequently used in cosmetic makeup materials, and well-known examples include surfactants in which the hydrophobic groups are hydrocarbons, such as sorbitan fatty acid esters, glycerin fatty acid esters, polyglycerin fatty acid esters, propylene glycol fatty acid esters, sucrose fatty acid esters, methyl glucoside fatty acid esters, alkyl polyglucosides, polyoxyalkylene fatty acid esters and polyoxyethylene hardened castor oil.

The use of hydrocarbon-based surfactants in combination with a silicone-based surfactant or the like within a water-in-oil emulsion is already known. For example, a hydrophilic polyoxyalkylene fatty acid ester, a sorbitan sesquioleate or a sorbitan sesquiisostearate or the like may be used in combination to improve the stability of the emulsion.

Thickeners

Of the cosmetic material components, there are no particular limitations on the thickeners that may be used, provided they are the types of thickeners typically used in cosmetic materials. These thickeners can be classified as aqueous-type thickeners and oil-type thickeners.

Examples of the aqueous-type thickeners include microparticulate silica; other inorganic powders such as bentonite and hectorite; and water-soluble polymers, including gum Arabic, guar gum, carrageenan, agar, quince seed, locust bean gum, xanthan gum, pullulan, sodium carboxymethylcellulose, hydroxyethylcellulose, vinyl-based polymers such as carboxyvinyl polymers, and acrylic polymers such as (ammonium acryloyldimethyltaurate/VP) copolymers, (Na acrylate/Na acryloyldimethyltaurate) copolymers, (hydroxyethyl acrylate/Na acryloyldimethyltaurate) copolymers and polyacrylamide.

Examples of the oil-type thickeners include hydrophobic microparticulate silica such as silylated silica, organic-modified clay minerals such as Disteardimonium Hectorite, metal soaps such as aluminum stearate, polysaccharide fatty acid esters such as dextrin (palmitate/2-ethylhexanoate) and inulin stearate, sucrose fatty acid esters such as sucrose acetate stearate, and crosslinked organopolysiloxanes.

Crosslinked organopolysiloxanes are compounds which, when combined with a liquid oil, undergo swelling by incorporating more than their own mass of the liquid oil. These crosslinked organopolysiloxanes may incorporate at least one portion selected from the group consisting of a polyoxyalkylene portions, polyglycerin portions, alkyl portions, alkenyl portions, aryl portions and fluoroalkyl portions. Examples of commercially available products of these crosslinked organopolysiloxanes include the KSG series of products (manufactured by Shin-Etsu Chemical Co., Ltd.) which are supplied in a paste-like form with an oil agent. These crosslinked organopolysiloxanes impart a dry feeling with minimal stickiness, and exhibit excellent thickening and stabilizing properties for oil-based and W/O type cosmetic materials.

Film-Forming Agents

Of the cosmetic material components, there are no particular limitations on the film-forming agents that may be used, provided they are the types of agents typically used in cosmetic materials. These film-forming agents can be classified as aqueous-type film-forming agents and oil-type film-forming agents.

Examples of materials that can be used as aqueous-type film-forming agents include emulsions and the like of polyvinyl alcohol, polyvinylpyrrolidone, vinyl acetate-vinylpyrrolidone copolymers and acrylic acid-based copolymers.

Examples of the oil-type film-forming agents include α-olefin-vinylpyrrolidone copolymers such as an eicosene-vinylpyrrolidone copolymers, acrylic acid-alkyl acrylate copolymers, silicone network resins such as trimethylsiloxy-silicic acid, and silicone network resins that further comprise a pyrrolidone portion, long-chain alkyl portion, polyoxyalkylene portion, fluoroalkyl portion, or anion portion such as a carboxylic acid within the molecular structure of the resin.

These film-forming agents may be selected in accordance with the intended purpose of the cosmetic makeup material, in order to improve the cosmetic retention of the material.

Other Ultraviolet Absorbers

Other ultraviolet absorbers besides the ethylhexyl methoxycinnamate of the above-mentioned component (d) may be used as required, and there are no particular limitations on these other ultraviolet absorbers, provided they are used in typical cosmetic materials. Examples include polysilicone-15, octocrylene, t-butylmethoxydibenzoylmethane, methylene bis(benzotriazolyl) tetramethylbutylphenol, octyl salicylate, homosalate, phenylbenzimidazole sulfonic acid, hydroxymethoxybenzophenone sulfonic acid, and octyl dimethyl PABA (2-ethylhexyl para-dimethylaminobenzoate).

Other Medicinal Agents

Examples of other medicinal agents that may be added to the cosmetic material according to need include antioxidants such as tocopherol; amino acids and derivatives thereof such as glycine, serine, alginine and glutamic acid; vitamins and derivatives thereof, including A vitamins such as vitamin A oil and retinol, B vitamins such as pyridoxine hydrochloride, panthenol, pantothenyl ethyl ether, nicotinamide and cyanocobalamin, C vitamins such as ascorbic acid palmitate and ascorbic acid glucoside, E vitamins such as α-tocopherol, and other vitamins such as nicotinic acids; and anti-inflammatory agents such as dipotassium glycyrrhizinate.

The present invention relates to a water-in-oil type cosmetic makeup material, and examples of cosmetic products in which the present invention can be used include wrinkle concealing cosmetic materials, makeup bases, concealers, liquid foundations, cream foundations, eye shadow, eyebrow products, and similar products that also provide a sunscreen effect.

EXAMPLES

The present invention is described in further detail below based on a series of examples, but the present invention is in no way limited by these examples. Unless stated otherwise, the units for the blend amounts in the following examples are % by mass.

Example 1

Comparative Examples 1 to 3

Water-in-oil type foundations were prepared using the formulations (units: % by mass) shown in Table 1.

TABLE 1

| Name of component | Example 1 | Comparative example 1 | Comparative example 2 | Comparative example 3 |
|---|---|---|---|---|
| 1 Crosslinked organopolysiloxane gel (Note 1) | 1.0 | 1.0 | 1.0 | 1.0 |
| 2 (b) Acrylic silicone-based graft copolymer solution (Note 2) | 2.0 | 2.0 | — | 2.0 |
| 3 Hydrophobically treated color pigment (Note 3) | 7.0 | 7.0 | 7.0 | 7.0 |
| 4 (a) Crosslinked polyether-modified silicone gel (Note 4) | 3.0 | — | 3.0 | 3.0 |
| 5 (c) Branched silicone surfactant (Note 5) | 0.1 | 0.1 | 2.1 | — |
| 6 Crosslinked organopolysiloxane gel (Note 6) | 3.0 | 3.0 | 3.0 | 3.0 |
| 7 Methylpolysiloxane (Note 7) | 8.2 | 11.2 | 8.2 | 8.3 |
| 8 Cyclopentasiloxane | 2.5 | 2.5 | 2.5 | 2.5 |
| 9 1,3-butylene glycol | 5.0 | 5.0 | 5.0 | 5.0 |
| 10 Sodium citrate | 0.2 | 0.2 | 0.2 | 0.2 |
| 11 Magnesium sulfate | 0.5 | 0.5 | 0.5 | 0.5 |
| 12 Preservative | suitable amount | suitable amount | suitable amount | suitable amount |
| 13 Pure water | remainder | remainder | remainder | remainder |
| Total | 100.0 | 100.0 | 100.0 | 100.0 |

Note 1: manufactured by Shin-Etsu Chemical Co., Ltd., KSG-16 (methylpolysiloxane gel, polymer fraction: approximately 25% by mass)
Note 2: manufactured by Shin-Etsu Chemical Co., Ltd., KP-545 (30% by mass solution of (alkyl acrylate/dimethicone) copolymer in cyclopentasiloxane)
Note 3: manufactured by Shin-Etsu Chemical Co., Ltd., a mixed product of KF-9909-treated color pigment
Note 4: manufactured by Shin-Etsu Chemical Co., Ltd., KSG-210 (a 25% by mass gel of (dimethicone/(PEG-10/15)) crosspolymer in methylpolysiloxane)
Note 5: manufactured by Shin-Etsu Chemical Co., Ltd., KF-6028P (PEG-9 polydimethylsiloxyethyl dimethicone)
Note 6: manufactured by Shin-Etsu Chemical Co., Ltd., KSG-15 (cyclopentasiloxane gel, polymer fraction: approximately 7%)
Note 7: manufactured by Shin-Etsu Chemical Co., Ltd., KF-96A, 6 cs (Production Method)

Components 4 to 8 were mixed and dispersed uniformly using a disper mixer, thus forming a mixture. Separately, components 9 to 13 were dissolved uniformly to prepare a solution. The solution was added gradually to the above mixture while emulsification was performed using a disper mixer, thus yielding an emulsion. A crushed powder that had been prepared separately by crushing the components 1 to 3 using a triple roll mill was then mixed uniformly into the emulsion with a disper mixer, thus yielding the targeted water-in-oil type foundation.

The thus obtained foundations of the example and the comparative examples were investigated for the following properties.

(1) Spreadability, Stickiness, Water-Releasability

The foundations obtained above were each evaluated for these feeling-based properties by 10 specialist panelists, using the criteria listed below.

Feeling of spreadability
 5 points: Very good spreadability
 4 points: Fairly good spreadability
 3 points: neither good nor poor spreadability
 2 points: Slightly poor spreadability
 1 point: Poor spreadability
Feeling of stickiness
 5 points: No stickiness
 4 points: Little stickiness
 3 points: neither good nor bad stickiness
 2 points: Slightly sticky
 1 point: Sticky Feeling of water-release
 5 points: feeling of bursting of water droplets
 3 points: almost no bursting occurs
 1 point: No water is noticeable The average value of the evaluations of the 10 panelists was ranked in the following manner. The ranking results are shown in Table 2.
 A: 4.5 points or higher
 B: at least 4.0 points but less than 4.5 points
 C: at least 3.0 points but less than 4.0 points
 D: less than 3.0 points (2) Stability Each of the foundations was stored for two months in a thermostatic chamber at 50° C., and the external appearance of the foundation was then evaluated visually, and the feeling-based properties were investigated by application to the skin. The results are shown in Table 2, with an "A" grade recorded for those foundations that exhibited no problems of product separation or a change in feeling, and a "D" grade for those foundations that did exhibit such problems.

(3) Pigment Dispersibility

Each of the foundations was inspected under an optical microscope (magnification: ×200), and the dispersion state of the pigment was evaluated. The results are shown in Table 2, with an "A" grade recorded for those foundations that had a favorable dispersion state, and a "D" grade recorded for those foundations for which the dispersion state was unsatisfactory due to the appearance of large aggregate lumps or the like among the pigment particles.

TABLE 2

| | Example 1 | Comparative example 1 | Comparative example 2 | Comparative example 3 |
|---|---|---|---|---|
| Stability | A | D | A | D |
| Pigment dispersibility | A | A | A | A |
| Feeling (spreadability) | B | C | B | B |
| Feeling (stickiness) | B | B | C | B |
| Feeling of water-release | A | A | D | A |

Evaluations: When the component (a) was not added, as in comparative example 1, emulsification tended to be difficult, even during the emulsification process, and the stability of the product was poor. In comparative example 2, instead of adding the component (b), the component 5 which exhibits excellent pigment dispersibility was added to ensure favorable dispersion of the pigment. Although the pigment dispersion was good, the feeling of water-release was lost. Comparative example 3 confirmed that the small amount of the component (c) was important for stability.

Example 2

A water-in-oil type foundation was prepared using the formulation listed below.

(Production Method)

Components 4 to 9 were mixed and dispersed uniformly using a disper mixer, thus forming a mixture. Separately, components 10 to 14 were dissolved uniformly to prepare a solution. The solution was added gradually to the above mixture while emulsification was performed using a disper mixer, thus yielding an emulsion. A kneaded product that had been prepared separately by kneading the components 1 to 3 using a triple roll mill was then mixed uniformly into the emulsion with a disper mixer, thus yielding the targeted water-in-oil type foundation.

| | Component | % by mass |
|---|---|---|
| 1 | Crosslinked organopolysiloxane gel (Note 1) | 1.0 |
| 2 | (b) Acrylic silicone-based graft copolymer solution (Note 2) | 2.0 |
| 3 | Hydrophobically treated color pigment (Note 3) | 7.0 |
| 4 | (a) Crosslinked polyether-modified silicone gel (Note 8) | 3.75 |
| 5 | (c) Branched silicone surfactant (Note 5) | 0.1 |
| 6 | Crosslinked organopolysiloxane gel (Note 6) | 3.0 |
| 7 | Methylpolysiloxane (Note 7) | 0.95 |
| 8 | (e) Phenyl-modified silicone (Note 9) | 6.5 |
| 9 | (d) Ethylhexyl methoxycinnamate | 3.0 |
| 10 | 1,3-butylene glycol | 4.7 |
| 11 | Sodium citrate | 0.2 |
| 12 | Magnesium sulfate | 0.5 |
| 13 | Preservative | 0.3 |
| 14 | Pure water | 67.0 |

(Note 8):
manufactured by Shin-Etsu Chemical Co., Ltd., KSG-240
(Note 9):
manufactured by Shin-Etsu Chemical Co., Ltd., KF-56A (Diphenylsiloxyphenyl Trimethicone)

The thus obtained foundation was not sticky, exhibited favorable spreadability and pigment dispersibility, and released water favorably upon application.

Samples of the foundation were left sitting for at least two months at 50° C. and at room temperature respectively, and both samples displayed good stability.

The above results confirmed that ethylhexyl methoxycinnamate was able to be added stably to the cosmetic material of the present invention. Moreover, by altering the amount of the component (e) and altering the amounts of the external oil phase and the internal water phase, the blend amount of the ethylhexyl methoxycinnamate can be increased.

Further, although the examples described above are foundations, other cosmetic makeup materials such as eye shadow, cosmetic material bases and cheek cosmetic materials can be prepared by altering the color of the hydrophobically treated color pigment used as the component 3.

As described above, the water-releasing cosmetic material of the present invention can be used for various cosmetic makeup materials, for the purposes of base makeup and point makeup.

What is claimed is:

1. A water-releasing cosmetic makeup material, formed of a water-in-oil emulsion comprising:
   (a) a partially crosslinked polyether-modified silicone, a partially crosslinked polyglycerin-modified silicone, or a combination thereof,
   (b) an acrylic silicone-based graft copolymer, and
   (c) 0.05 to 0.7% by mass of a branched silicone surfactant which is a silicone compound represented by general formula (1):

$$R^1_a R^2_b R^3_c SiO_{(4-a-b-c)/2} \qquad (1)$$

wherein a, b, and c are numbers that satisfy ranges $1.0 \leq a \leq 2.5$, $0.001 \leq b \leq 1.5$, and $0.001 \leq c \leq 1.5$, respectively, and each $R^1$ represents an identical or different organic group selected from the group consisting of alkyl groups, aryl groups, aralkyl groups and fluorine-substituted alkyl groups of 1 to 30 carbon atoms, and organic groups represented by general formula (2):

$$-C_m H_{2m}-O-(C_2H_4O)_d(C_3H_6O)_e R^4 \qquad (2)$$

wherein m represents an integer that satisfies $0 \leq m \leq 15$, d and e are integers that satisfy ranges $0 \leq d \leq 50$ and $0 \leq e \leq 50$, respectively, and $R^4$ represents a hydrogen atom, a hydrocarbon group of 4 to 30 carbon atoms or an organic group represented by $R^6-(CO)-$, $R^2$ represents a polyoxyalkylene group represented by general formula (3):

$$-C_m H_{2m}-O-(C_2H_4O)_f(C_3H_6O)_g-R^5 \qquad (3)$$

wherein m represents an integer that satisfies $0 \leq m \leq 15$, f and g are integers that satisfy ranges $2 \leq f \leq 200$ and $0 \leq g \leq 200$, respectively, provided that f+g satisfies a range of 3 to 200, and $R^5$ represents a hydrogen atom, a hydrocarbon group of 1 to 30 carbon atoms or an organic group represented by $R^6-(CO)-$, wherein $R^6$ represents a hydrocarbon group of 1 to 30 carbon atoms, and $R^3$ represents an organosiloxane residual group represented by general formula (4) below:

$$-C_n H_{2n}-(\underset{R^1}{\underset{|}{\overset{R^1}{\overset{|}{Si}}O}})_h-SiR^1_3, \qquad (4)$$

wherein n represents an integer that satisfies $1 \leq n \leq 5$ and h represents an integer that satisfies $0 \leq h \leq 500$.

2. The water-releasing cosmetic makeup material according to claim 1, further comprising:
   (d) ethylhexyl methoxycinnamate.

3. The water-releasing cosmetic makeup material according to claim 2, further comprising:
   (e) a phenyl-modified silicone.

4. The water-releasing cosmetic makeup material according to claim 1, wherein component (a) is a partially crosslinked polyether-modified silicone.

5. The water-releasing cosmetic makeup material according to claim 1, comprising:
   (a) 0.5 to 1.5% by mass of a partially crosslinked polyether-modified silicone, a partially crosslinked polyglycerin-modified silicone, or a combination thereof, and
   (b) 0.3 to 1.5% by mass of an acrylic silicone-based graft copolymer.

6. The water-releasing cosmetic makeup material according to claim 3, wherein a blend amount of the ethylhexyl methoxycinnamate of component (d) is not more than a blend amount of the phenyl-modified silicone of component (e) on a mass % basis.

7. The water-releasing cosmetic makeup material according to claim 1, wherein the cosmetic makeup material is a water-in-oil type foundation.

8. The water-releasing cosmetic makeup material according to claim 1, wherein the branched silicone surfactant of component (c) is a silicone compound represented by general formula (1):

     (1)

wherein each $R^1$ represents an identical or different organic group selected from the group consisting of alkyl groups, aryl groups, aralkyl groups and fluorine-substituted alkyl groups of 1 to 30 carbon atoms, $R^2$ represents a polyoxyalkylene group represented by general formula (3a):

     (3a)

$R^3$ represents an organosiloxane residual group represented by general formula (4) below:

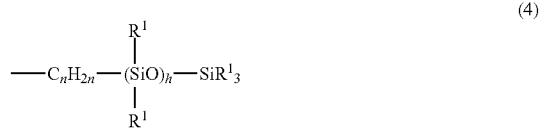     (4)

a, b and c are numbers that satisfy ranges $1.0 \leq a \leq 2.5$, $0.001 \leq b \leq 1.5$, and $0.001 \leq c \leq 1.5$, respectively, f is an integer that satisfies $3 \leq f \leq 200$, m represents an integer that satisfies $0 \leq m \leq 15$, and h represents an integer that satisfies $0 \leq h \leq 500$.

9. The water-releasing cosmetic makeup material according to claim 8, wherein each $R^1$ represents an alkyl group of 1 to 30 carbon atoms.

10. The water-releasing cosmetic makeup material according to claim 9, wherein each $R^1$ represents a methyl group.

* * * * *